United States Patent [19]

Hasegawa

[11] Patent Number: 4,941,457

[45] Date of Patent: Jul. 17, 1990

[54] ENDOSCOPE USING AN OPTICAL GUIDE TWISTED ON THE TIP SIDE TO HAVE THE VISUAL FIELD DIRECTION AND CURVATURE AXIS COINCIDE WITH EACH OTHER

[75] Inventor: Hiroshi Hasegawa, Hachioji, Japan

[73] Assignee: Olympus Optical Co., Ltd., Tokyo, Japan

[21] Appl. No.: 394,895

[22] Filed: Aug. 17, 1989

[51] Int. Cl.$^5$ .................... A61B 1/06; G01N 21/01
[52] U.S. Cl. .......................................... 128/6; 128/4; 356/241
[58] Field of Search .................. 128/6, 4; 356/241

[56] References Cited

U.S. PATENT DOCUMENTS 4,697,577 10/1987 Forkner .................................. 128/6
4,747,661 5/1988 Ohkuwa ............................ 128/6 X
4,809,680 3/1989 Yabe ..................................... 128/6

FOREIGN PATENT DOCUMENTS 61-21043 6/1986 Japan .
64-13023 1/1989 Japan .
1-137221 5/1989 Japan .

Primary Examiner—William H. Grieb
Attorney, Agent, or Firm—Armstrong, Nikaido, Marmelstein, Kubovcik & Murray

[57] ABSTRACT

As inserted through an insertable part, a flexible image guide transmitting an optical image and a flexible light guide transmitting an illuminating light are secured in a tip part so as to be parallel/vertical to a curvature axis and are inserted in a position displaced rotatably around the center axis within a curvable tube part adjacent to this tip part so that, in case a tip adapter is fitted, the visual field direction and the direction of the curvature axis may be parallel/vertical to each other.

13 Claims, 9 Drawing Sheets

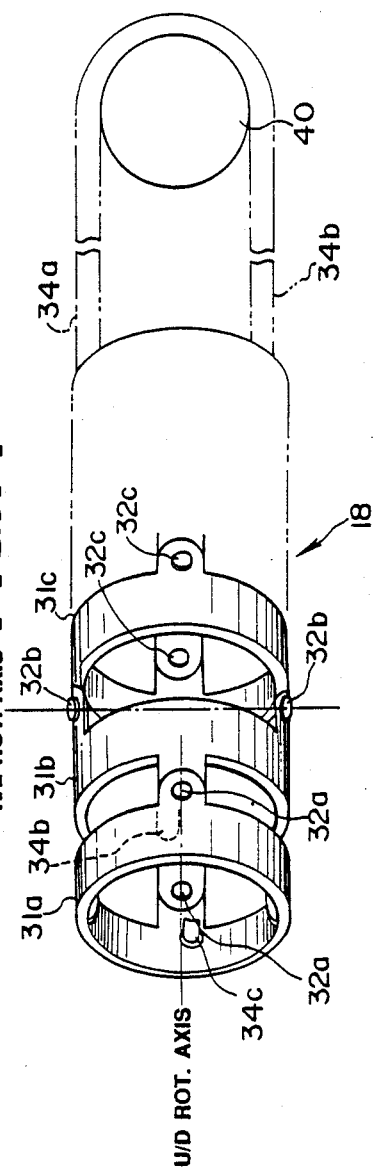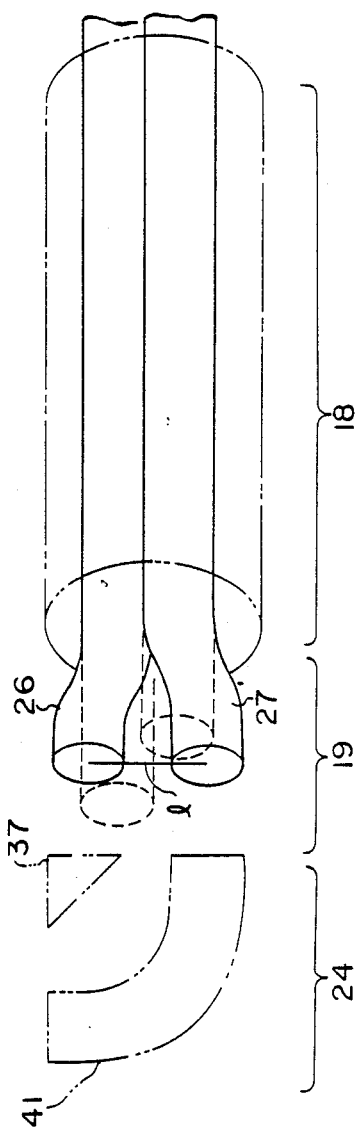

ENDOSCOPE USING AN OPTICAL GUIDE TWISTED ON THE TIP SIDE TO HAVE THE VISUAL FIELD DIRECTION AND CURVATURE AXIS COINCIDE WITH EACH OTHER

BACKGROUND OF THE INVENTION

1. Field of the Invention and Related Art Statement

This invention relates to an endoscope apparatus containing an image guide or light guide as twisted on the tip side to have the visual field direction and curvature axis coincide or intersect at right angles with each other.

Recently, there are used many (medical) endoscopes whereby an elongate insertable part is inserted into a body cavity so that organs within the body cavity may be observed and diagnosed without incising the body. Also, in the same manner, there are used (industrial) endoscopes whereby an elongate insertable part is inserted into an engine or a device of a plant or the like so that the interior of the engine or device may be observed or inspected.

A visual field direction changing adapter which changes the visual field direction of an objective lens in the tip forming part at the front end of an endoscope, for example, to a side viewing direction from a straight viewing direction can be removably fitted to such endoscope.

A prior art example of an endoscope apparatus provided with the above mentioned visual field direction changing adapter is suggested in a Japanese utility model application No. 106348/1987 and is shown in FIGS. 1 and 2.

Of the internal structure which is not shown in this prior art example but is considered to be such and is therefore mentioned as a related art example, the cross-section on A—A in FIG. 1 is shown in FIG. 3, the cross-section on B—B is shown in FIG. 4 and the view as seen in the direction of the arrow C is shown in FIG. 5. In these drawings, a tip forming part 3 is provided at the tip of an insertable part 1 through a curvable tube part 2 and is fitted with a visual field direction changing adapter 7. The above mentioned curvable tube 2 is made curvable in the four directions of U, D, R and L by a U/D (UP/DOWN) rotary axis shown in FIG. 3 and an R/L (RIGHT/LEFT) rotary axis intersecting at right angles with it. By the way, the curving operation is made by pulling one and relaxing the other of respective pairs of curving operation wires 6.

Within the above mentioned curvable tube part 2, an image guide fiber bundle 4 and light guide fiber bundle 5 are arranged on a straight line included by 45 degrees, for example, to the R/L rotary axis respectively in the spaces held by the adjacent curving operation wires 6. The image guide fiber bundle 4 and light guide fiber bundle 5 are fixed to the above mentioned tip forming part 3 substantially equally to this arrangement (See FIG. 4) and these fixing positions are in such position relation that the light guide fiber bundle 5 may be located on the X axis shown in FIG. 5 and passing through the center of the image guide fiber bundle 4 and the center of the tip forming part 3.

The above mentioned visual field direction changing adapter 7 is formed of an illuminating window 8 consisting of a prism and cover lens for changing the light path from the straight viewing to the side viewing of an illuminating optical system and an observing window 9 consisting of a prism and cover lens the same as in an observing optical system so that the visual field direction may be the same direction as of the above mentioned X axis (See FIG. 5).

As the image guide fiber bundle 4 and light guide fiber bundle 6 are housed as displaced from the U/D rotary axis or R/L rotary axis, there are merits that the structure shown in FIG. 3 can be made more compact than in the case that they are housed on these axes and therefore the outside diameter of the curvable tube part 2 can be made smaller.

However, in case the visual direction changing adapter 7 is fitted as in FIG. 1, the visual field direction will not coincide with the U/D rotary axis direction. In this related art example, the direction at 45 degrees with the U/D rotary axis direction is a visual field direction.

Therefore, when the curving operation is made, for example, in the U/D direction, in FIG. 3, the tip forming part 7 will rotatably move within a plane in which the center axis O includes that axis O and U/D rotary axis. In this case, as the visual field direction V is not included in the above mentioned plane, it will be difficult for the operator to anticipate where the visual field direction will be directed by the curving operation.

Therefore, such operation as, for example, of moving the part displaced from the center of the visual field to the center of the visual field will be difficult.

Also, in the case of changing the observing direction, the operation of setting it in a desired direction will be difficult. Such defects will be produced. The same problems will be produced also in the case of curving in the R/L direction.

2. Objects and Summary of the Invention

An object of the present invention is to provide an endoscope whereby the change of the visual field direction by the curving operation can be easily anticipated without making the curvable tube part thick.

Another object of the present invention is to provide an endoscope whereby the visual field direction can be changed or the like by fitting an adapter simple in the structure.

In the present invention, the tip side end parts of a light guide inserted through an insertable part and transmitting an illuminating light and of an image guide transmitting an optical image are secured so as to be parallel/vertical to the line connecting at least one pair of pivoting parts of a curvable tube part, are changed rotatably around the center- axis within the curvable tube part adjacent to this tip part and are inserted through positions away from the pivoting parts. Thus, both guides can be inserted through the curvable tube part without making it thick, in the case of fitting the tip adapter, the visual field direction and curvature axis direction can be made parallel/vertical and, in the case of the curving operation, the moving direction of the visual field can be easily anticipated. By using two image guides, a stereo-observation can be made. Further, in case a CCD is used instead of using the image guide, by twisting the signal line, the same effect will be obtained.

BRIEF DESCRIPTION OF THE DRAWINGS

FIG. 3 is a sectioned view considered to be of a cross-section on line A—A in FIG. 1.

FIG. 4 is a sectioned view considered to be of a cross-section on line B—B in FIG. 1.

FIG. 5 is an elevation as seen in the C direction in FIG. 1.

FIGS. 6 to 15 relate to the first embodiment of the present invention.

FIG. 7 is a sectioned view showing the structure of a visual field direction changing adapter.

FIG. 8 ia a perspective view showing the contour of an endoscope of the first embodiment.

FIG. 9 is a side view showing the tip side as fitted with a visual filed direction changing adapter.

FIG. 10 is a plan view of FIG. 9.

FIG. 11 is a magnified sectioned view on line D—D in FIG. 9.

FIG. 12 is a magnified sectioned view on line E—E in FIG. 9.

FIG. 13 is a magnified elevatin as seen in the F direction in FIG. 9.

FIG. 14 is a perspective view showing the formation of a curvable tube part.

FIG. 15 is a perpective view schematically showing that the image guide and light guide are twisted near the tip.

DETAILED DESCRIPTION OF THE PREFERRED EMBODIMENTS

Figure 8:
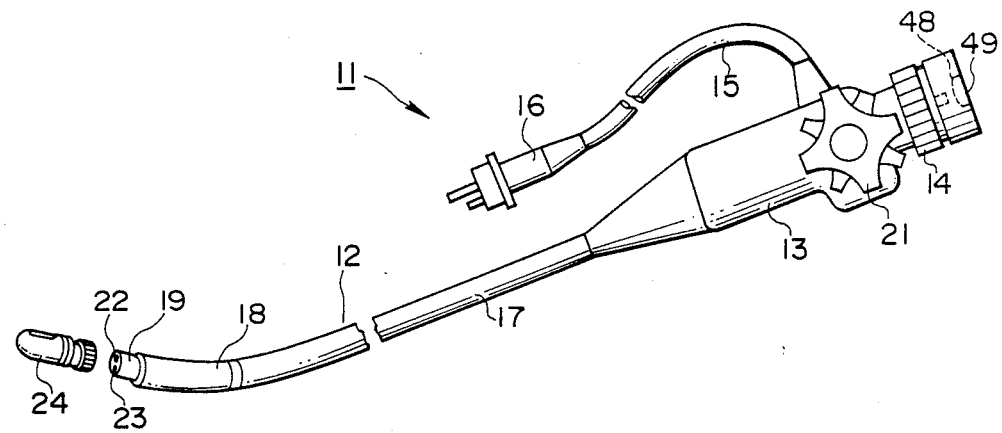

As shown in FIG. 8, an endoscope 11 of the first embodiment comprises an elongate insertable part 12, an operating part connected to the rear end of this insertable part 12, an eyepiece part 14 provided at the rear end of this operating part 13 and a universal cord 15 extended out of the side of the above mentioned operating part 13.

A connector 16 connectable to a light source apparatus not illustrated is fitted to the end of the above mentioned universal cord 15.

The above mentioned insertable part 12 is formed of an elongate flexible tube part 17 formed of a soft member, a curvable tube part 18 formed at the front end of this flexible tube 17 and a rigid tip forming part 19 formed at the front end of this curvable tube part 18. This curvable tube part 18 can be curved in four upward, downward, rightward and leftward directions.

An observing window 22 and illuminating window 23 are provided on the tip surface of the above mentioned tip forming part 19.

Figure 9:
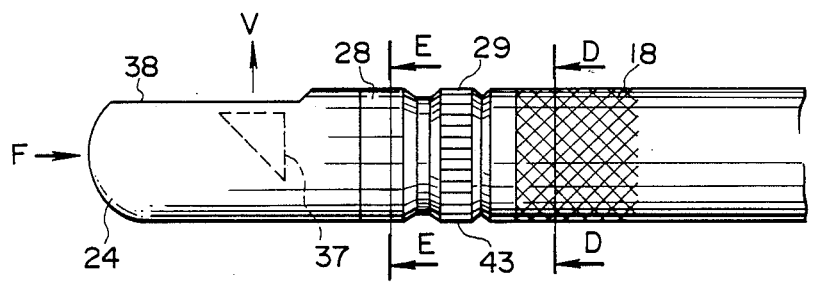
Figure 10:
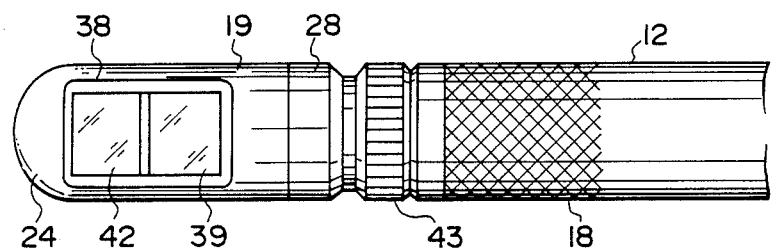

A visual field direction changing adapter 24 for changing the observing direction (visual field direction) from the straight viewing direction (forward direction along the lengthwise direction of the tip part 19) to the side viewing direction can be removably fitted to this tip (forming) part 19. This visual field direction changing adapter 24 as fitted is as shown in FIGS. 9 and 10.

Figure 6A:
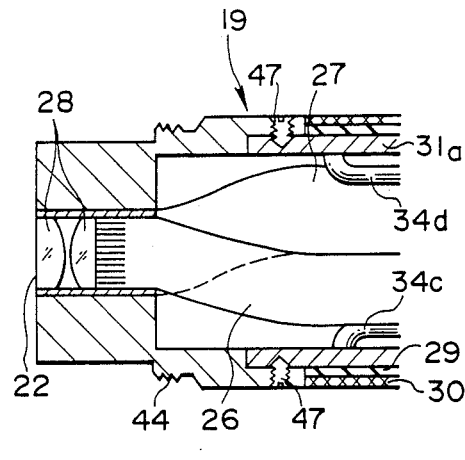
FIGS. 6a and 6b are sectioned views respectively in the horizontal direction and vertical direction showing the arranged structures of an image guide and light guide on the tip part side.
Figure 11:
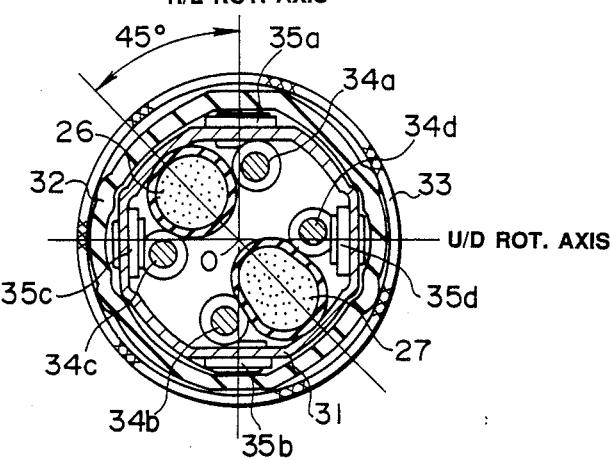

As shown in FIGS. 6 and 11, a flexible image guide fiber bundle 26 for transmitting an optical image and a flexible light guide fiber bundle 27 for transmitting an illuminating light are inserted through the above mentioned insertable part 12. As shown in FIG. 6, objective lenses 28 are fitted in front of the entrance end surface of this image guide fiber bundle 26 so that an image may be formed on the entrance end surface of the image guide fiber bundle 26 by these objective lenses 28.

The optical image transmitted by the above mentioned image guide fiber bundle 26 can be magnified and observed from an eyepiece window 49 through an eyepiece lens 48 arranged as opposed to the other end surface.

The foremost step one of articulated frames 31 forming the curvable tube part 18 is secured to the rear end of the above mentioned tip part 19 and is covered on the outside, for example, with a flexible tube 29 and net tube 30.

As shown in FIG. 14, the curvable tube part 18 is formed by rotatably connecting in the lengthwise direction many ring-like articulated frames 31a, 31b, . . .

A projecting piece projected in two opposed places (in the illustration, in two places in the horizontal direction), for example, at the rear end of the joint frame 31a and a projecting piece projected at the front end of the articulated frame 31b adjacent to this articulated frame 31a are respectively rotatably pivoted by rivets 32a so that the articulated frames 31a and 31b may be rotatable around the line connecting the rivets 32a which are to be pivoting parts.

Also, at the rear end of the articulated frame 31b, projecting pieces are projected in two opposed places intersecting at right angles with the direction in which the above mentioned projecting pieces are provided, that is, in two places in the vertical direction and are rotatably connected by rivets 32b with projecting pieces at the front end of the articulated frame 31c adjacent to this articulated frame 31b by rivets 32b so that the articulated frames 31b and 31c may be rotatable around the line connecting the rivets 32b which are to be pivoting parts.

The curvable tube 18 is made curvable fundamentally in the vertical and horzontal directions by the above mentioned three articulated frames 31a, 31b and 31c but the curvable quantity is so small that many articulated frames are connected also in the rear of the articulated frame 31c.

Respective pairs of wires 34c and 34d and of wires 34a and 34b are secured at the tips to the foremost step articulated frame 31a in the direction substantially equal to the pivoted direction, that is, in two places in the horizontal direction and in two places in the vertical direction. For example, the wire 34a (34b) is inserted along the pivoting part in the vertical direction inside the articulated frames 31a, 31b, 31c . . . In this case, the inserted position is prevented by such ring-like wire guide 33a (33b) as is shown in FIG. 11 from being displaced. One pair of wires 34a and 34b are to make a cuvature in the vertical direction and are wound up on a drum 40 connected with an angle knob 21 of the operating part 13 so that, when the angle knob 21 is rotated, this drum 40 will rotate. When one wire (for example, 34a) is pulled and the other wire (34b) is relaxed, the articulated frame 31a will curve in the upward direction or downward direction with the line connecting a pair of pivoting parts, that is, the rivets 32a as a U/D rotary axis. (The articulated frame 31c will also curve in the same manner with the line connecting the rivets 32c as a U/D rotary axis.) The other pair of wires 34c and 34d are to make a curvature in the horizontal direction and are of the same formation as of the wires 34a and 34b except that the direction is different. Therefore, when one of the wires 34c and 34d is pulled and the other of them is relaxed, for example, the articulated frame 31b will be able to be curved in the rightward direction or leftward direction with the line connecting the rivets 32b as an R/D roatry axis.

Figure 7:
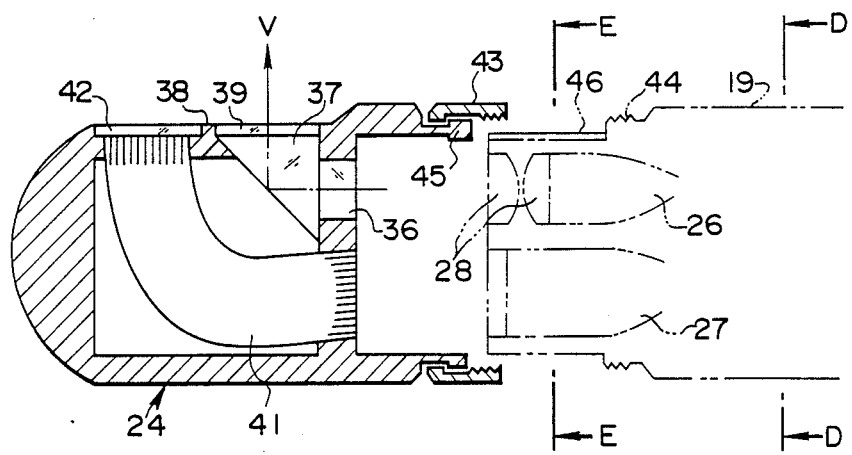

Now, the visual field direction changing adapter 24 fittable to the tip part 19 is of a structure shown, for example, in FIG. 7. An optical rod 36 is fitted as opposed to the objective lenses 28 and a rectangular prism 37 is fitted to the front surface of this optical rod 36 to form a visual field changing optical system with which a sidewise visual field direction V can be obtained through a cover lens 39 fitted to the flat side surface 38. One end surface of a bent light guide fiber bundle 41 is located as opposed to the exit end surface of the light guide fiber bundle 27 so that the illuminating light may be emitted sidewise further through a cover glass 42 from the exit end surface facing the side surface.

A recess is provided in the peripheral direction on the outer periphery on the base end side of this visual field direction changing adapter 24 so that, when an adaptor ring 43 whose projection is engaged with this recess is screwed to a screw part 44 on the tip part 19 side, the visual field direction changing adapter 24 may be fitted to the tip part 19. BY the way, a projection 45 projecting inside in the radial direction is provided in one place of the base end part of this adapter 24 and, on the other hand, a groove part 46 in which this projection 45 can be engaged is Provided in the tip part 19 so that positioning may be made in fitting.

Now, in this first embodiment, the image guide fiber bundle (mentioned as the IG fiber bundle hereinafter) 26 and light guide fiber bundle (mentioned as the LG fiber bundle hereinafter) 27 inserted through the insertable part 12 are passed through a space partitioned with four wires 34a to 34d as shown in FIG. 11. The two fiber bundles 26 and 27 are provided so as to be arranged on a straight line inclined to the R/L rotary axis, for example, by 45 degrees. By such arrangement, the outside diameter of the insertable part 12 (curvable tube part 18) need not be made thick.

Figure 12:
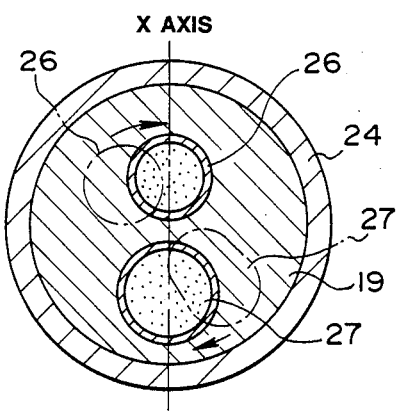
Figure 13:
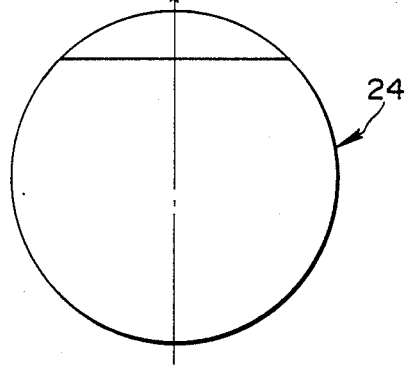

In the position before the foremost step articulated frame 31a to which these wires 34a to 34d are fixed at the tips, as understood from the comparison of FIGS. 11 and 12, the IG fiber bundle -6 and LG fiber bundle 27 are moved in the direction reverse to each other, that is, twisted around the center axis O and are fixed to the tip part 19 so that the centers of the respective tip surfaces of the bundles may be arranged, for example, on the R/L rotary axis.

In incorporating the bundles in this structure, for example, in FIG. 6, both IG and LG fiber bundles are fixed at the tips to the tip part 19 by soldering or screwing and then this tip part body 19 may be twisted, for example, by 45 degrees with respect to the articulated frame 31a side and may be fixed by screwing 47 or soldering. Thus, the structure of twisting both fiber bundles 26 and 27 can be simply made.

By the way, in FIG. 12, the one-point chain lines show the positions of the IG fiber bundle 26 and LG fiber bundle 27 on the curvable tube part 18 side. In FIGS. 11 and 12, the IG fiber bundle 26 and LG fiber bundle 27 are covered with flexible tubes which are omitted in FIG. 6.

It is shown in FIG. 15 that the IG fiber bundle 6 and LG fiber bundle 27 are twisted in the part from the tip part 19 to the curvable tube part 18.

The line l connecting the centers of both fiber bundles 26 and 27 is parallel with the R/L rotary axis of the line connecting the rivets 32b and intersects at right angles with the U/P rotary axis of the line connecting the rivets 32a. Therefore, when one of the wires 34c and 34d for the rotation with this R/L rotary axis is pulled and the other is relaxed, the curvable part will be able to be curved in the R/L direction a plane intersecting at right angles with the line and including the center axis O.

Therefore, when, as shown in FIG. 7, the prism 37 or LG fiber bundle 41 is arranged with the light leading direction changed within the same plane, the adapter 24 will be able to hold the main axis of the curvature axis and the visual field direction as coinciding with each other.

Therefore, it is easy to anticipate the direction in which the visual field will change in case the curving is operated.

Figure 1:
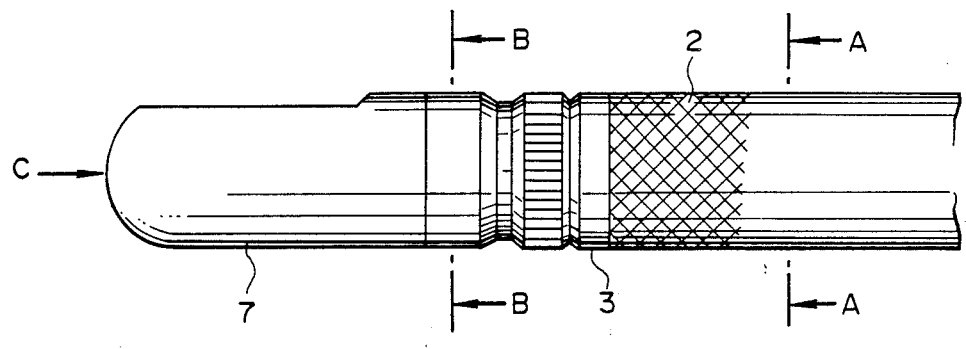
FIG. 1 is a side view showing the tip side in a prior art example.
Figure 2:
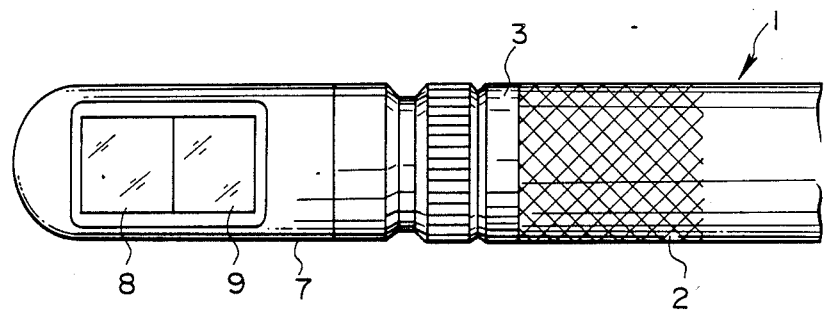
FIG. 2 is a plan view of FIG. 1.
Figure 3:
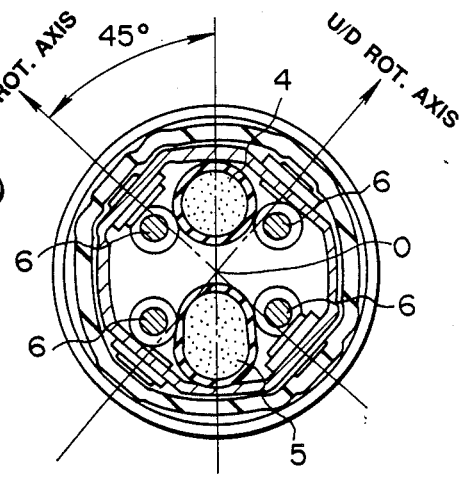
FIGS. 3 to 5 relate to a related art example.
Figure 4:
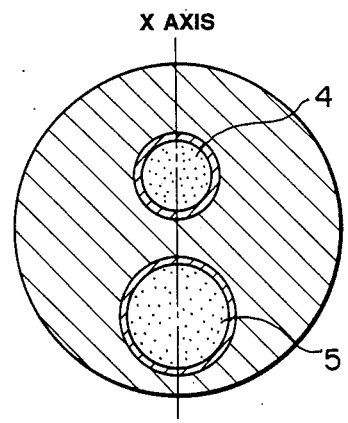
Figure 5:
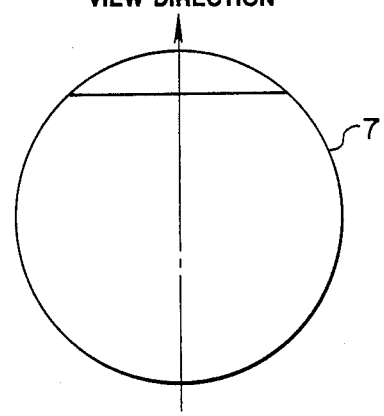

On the other hand, in case both fiber bundles 26 and 27 are not twisted as shown by the dotted lines in FIG. 15, as the visual field direction and the main axis of the curvature axis do not coincide with each other as described in FIGS. 3 to 5, it will be difficult to anticipate the visual field direction in case the curving operation is made. In order to dissolve it, the prism 37 and LG fiber bundle 41 may be housed as twisted in the adapter 24. However, it is difficult to twist the led light particularly on the prism 37 side.

As described above, according to this first embodiment, the IG fiber bundle 26 and LG fiber bundle 27 are moved so as to be rotated, for example, around the center axis O of the tip part 19 in the positions foward of the tips of the wires 34a to 34d and are fixed so that the center positions of the tip surfaces of the IG fiber bundle 26 and LG fiber bundle 27 may be arranged, for example, on the R/L rotary axils. The visual field direction V of the visual field direction changing adapter 24 fitted to this tip part 19 is made to be in the same direction as the above mentioned X axis.

According to the first embodiment of such structure, when the visual field direction changing adapter 24 is fitted, the curved UP direction and visual field direction will be able to be made to coincide with each other and, in the case of curving and moving the adapter to the object position while seeing the observed visual field, the variation of the visual field direction by the curving operation will be easy to anticipate. Therefore, the operation of setting the objective position, for example, in the center of the visual field will be easy.

Figure 16:
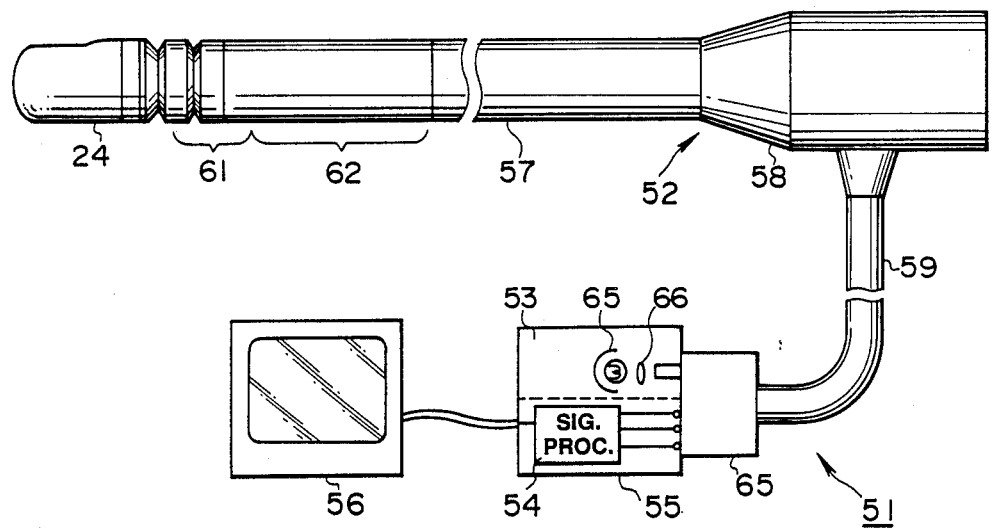
FIG. 16 is a general formation view of an electronic endoscope apparatus provided with the second embodiment of the present invention.

FIG. 16 shows an electronic endoscope apparatus 51 provided with the second embodiment of the present invention.

This apparatus 51 comprises an electronic endoscope 52, a video processor 55 having a light source part 53 for feeding an illuminating light to this electronic endoscope 52 and a signal processing circuit 54 for processing signals built-in and a color monitor 56 for displaying a standard video signal produced in this signal processing circuit 54.

The above mentioned electronic endoscope 52 has a thick operating part 58 formed at the rear end of an elongate insertable part 57 and has a universal cord 59 extended out of this operating part 58.

A rigid tip part 61 is formed at the tip of the above mentioned insertable part 57 and a curvable tube part 62 is formed in the rear of the tip part part 61.

The adapter 24 explained in the first embodiment can be fitted to the above mentioned tip part 61.

Figure 17:
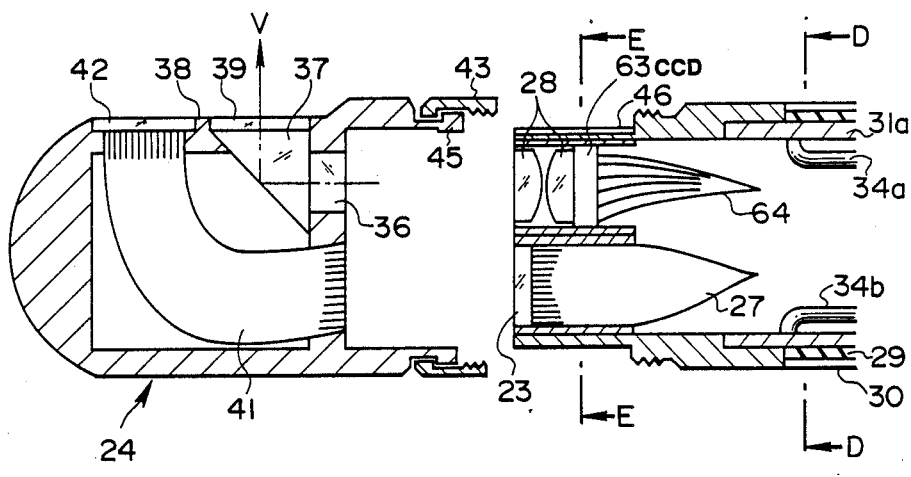
FIG. 17 is a sectioned view showing the structure on the tip side of the electronic endoscope of the second embodiment.

This tip part 61 is of such structure as is shown in FIG. 17.

That is to say, in FIG. 17, not the image guide 26 but a CCD 63 is arranged in the focal plane of the objective lens 28. Signal lines 64 are connected to this CCD 63, are inserted through the insertable part 57, are then further inserted through the universal cord 59 through the operating part 58 and are connected with the signal processing circuit 54 through a connector 65. The above mentioned signal lines 64 and LG fiber bundle 27 are housed within the insertable part the same as in the first embodiment.

That is to say, the sectioned views on lines D—D and E—E in FIG. 17 are respectively as in FIGS. 11 and 12. However, the image guide 26 in FIGS. 11 and 12 is replaced with the signal lines 64.

By the way, a white color light of a lamp 65 forming the light source part 53 is condensed by a lens 66 and is fed to the end part of the light guide 27 inserted through the universal cord 59.

The operation and effect of this second embodiment are substantially the same as of the first embodiment.

Figure 18:
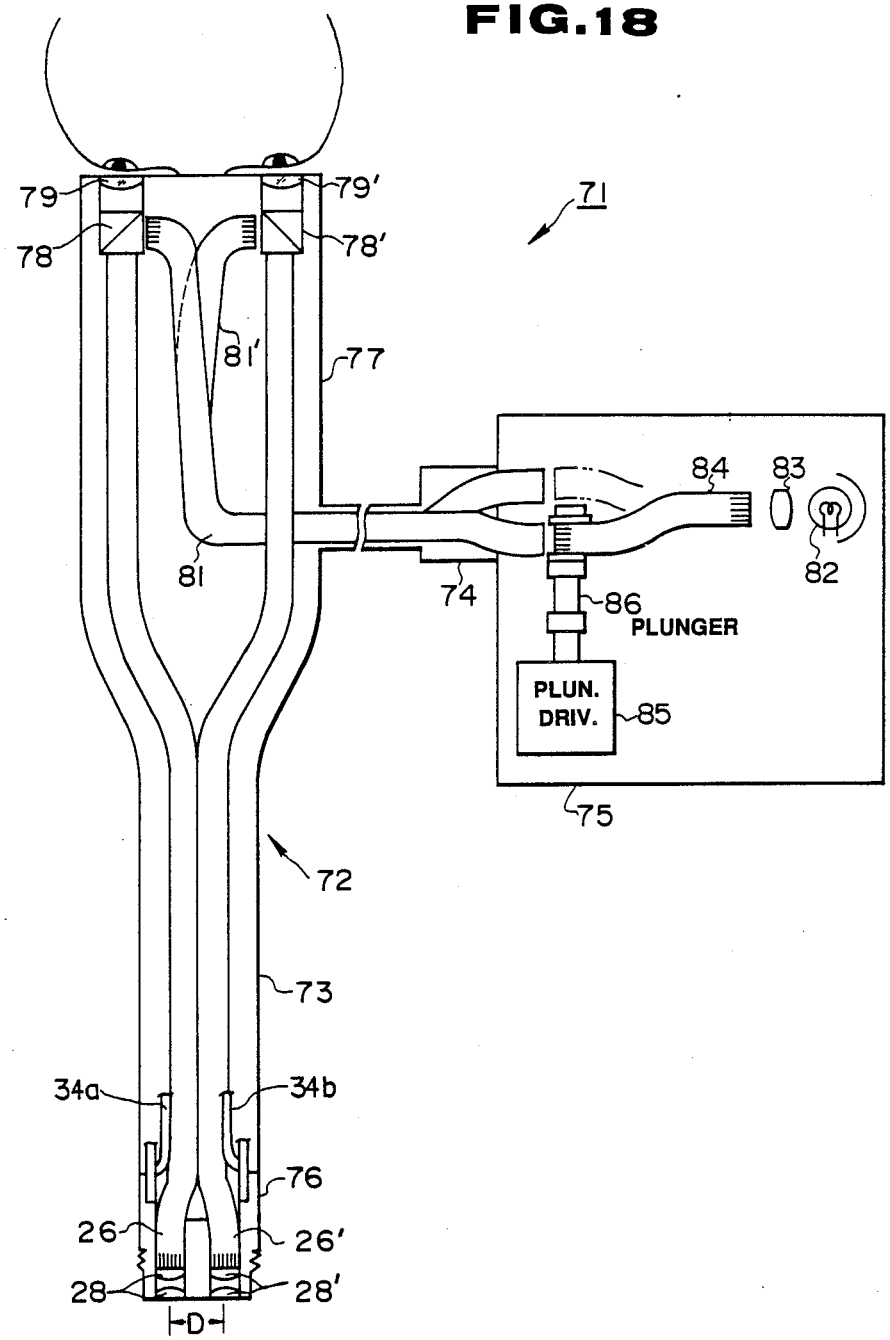
FIG. 18 is a general formation view of a stereo-endoscope provided with the the third embodiment of the present invention.

FIG. 18 shows a stereo-endoscope apparatus 71 provided with the third embodiment of the present invention. As shown in FIG. 18, the stereo-endoscope apparatus 71 comprises a stereo-endoscope 72 having an elongate insertable part and a light source apparatus 75 feeding an illuminating light by fitting a connector of this stereo-endoscope 72.

Two objective optical systems 28 and 28' are secured to the tip part 76 of the above mentioned insertable part 73 so that the end surfaces of IG fiber bundles 26 and 26' may face the respective focal planes. These IG fiber bundles 26 and 26' are inserted through the insertable part 73 and are then further extended to beam splitters 78 and 78' of an operating eyepiece part 77.

Optical images transmitted through the above mentioned IG fiber bundles 26 and 26' can be observed through eyepiece lenses 79 and 79' arranged as opposed to the beam splitters 78 and 78'.

The end surfaces on one side of light guides 81 and 81' are arranged as opposed to the other surfaces of the above mentioned beam splitters 78 and 78' so that an illuminating light fed to the end surfaces on the connector 74 side may be fed to the IG fiber bundles 26 and 26' through the beam splitters 78 and 78.

Now, the light source apparatus 75 feeds a white color illuminating light of a lamp 82 to one end surface of a light guide 84 through a lens 83. The other end part of this light guide 84 is secured to a plunger 86 reciprocated by a plunger driving mechanism 85 so as to feed the transmitted illuminating light alternately to the respective end surfaces of the light guides 81 and 81'.

Therefore, at a timing, the state shown in FIG. 18 will be made, the illuminating light will be fed to the IG fiber bundle 26 through the light guides 84 and 81 and will illuminate the object through the objective lens 28 and an image of the illuminated object will be formed on one end surface of the other IG fiber bundle 26' by the other objective lens 28', will be transmitted to the other end surface by this IG fiber bundle 26' and will be able to be observed through the beam splitter 78' and eyepiece lens 79'.

At the next timing, as shown by the two-point chain lines, the light guide 84 will be opposed to the end surface of the other light guide 81', in this state, the illuminating light will be transmitted by the IG fiber bundle 26' and the other IG fiber bundle 26 will transmit an optical image.

Thus, in case one of the two IG fiber bundles 26 and 26' is acting as a light guide transmitting the illuminating light, the other will act to transmit the optical image so that, when these actions are switched, a stereoscopic observation may be made by the eyepiece lenses 79 and 79'.

Figure 19:
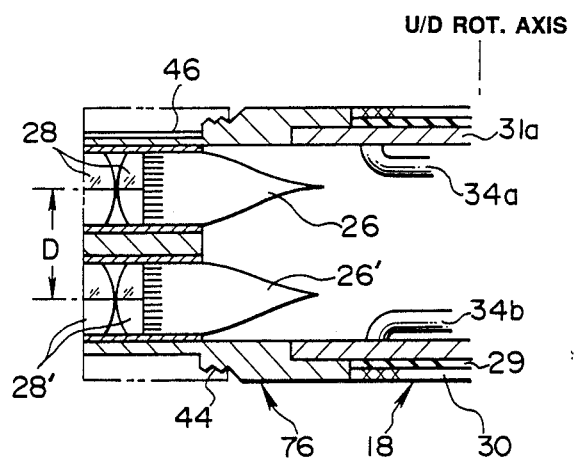
FIG. 19 is a sectioned view showing the structure on the tip side of the stereo-endoscope of the third embodiment.

Now, the structure of the tip side of the insertable part 73 is as shown in FIG. 19.

Figure 6B:
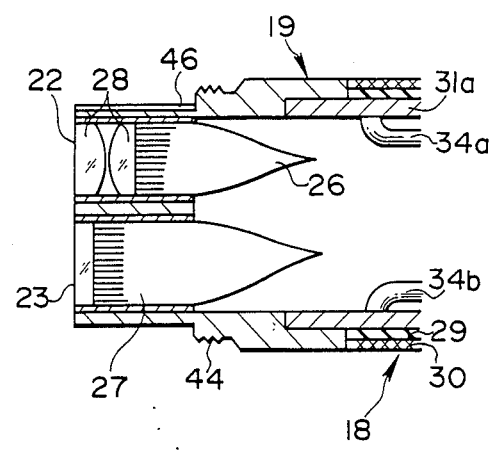

The structure shown in FIG. 19 is that, in FIG. 6b, the LG fiber bundle 27 is replaced with the objective lens 28' and IG fiber bundle 26' of the same characteristics as of the IG fiber bundle 26. Also, in this embodiment, the direction in which the two IG fiber bundles 26 and 26' are fixed is made a direction intersecting at right angles with the direction in FIG. 6b. Therefore, the line connecting the optical axes of these IG fiber bundles 26 and 26' intersects at right angles with the R/L rotary axis. The others are of the same formation as is shown in FIG. 6b. That is to say, the line connecting the center axes of the tips of the two IG fiber bundles 26 and 26' intersects at right angles with the line connecting the rivets 32a (when FIG. 14 is used), that is, the R/L rotary axis and coincides with the line connecting the rivets 32b, that is, the U/D rotary axis. (As the direction in which the two IG fiber bundles 26 and 26' are fixed is different by 90 degrees from that in the first embodiment, in this third embodiment, the line connecting the rivets 32a shown in FIG. 14 is the R/L rotary axis.)

In this third embodiment, in FIGS. 18 or 19, the distance D between the optical axes of the two objective lenses 26 and 26' will be a parallax with which the object can be stereoscopically observed. Therefore, in case the affected part or the like is swollen, if this stereo-endoscope 72 is used, the swollen manner or the like will be easy to recognize so as to be convenient in diagnosing or the like.

Also, in this stereo-endoscpe 72, as the parallax foming direction and the R/L rotary axis are intersected at right angles with each other, one of the wires 34a and 34b for the R/L curving shown in FIG. 19 will be pulled and the other will be relaxed and therefore the tip part 76 can be curved rightward or leftward in the direction intersecting at right angles with this R/L rotary axis, that is, within the plane (coinciding with this paper surface) including both optical axes in FIG. 19. That is to say, the direction of the stereoscopically observing optical system can be changed the same as in the human sight structure. By the way, even in case the curving operation in the vertical direction is made, the plane including both optical axes will be able to be curved in the upward direction or downward direction.

Therefore, in case a curving operation is made, the direction in which the visual field will move will be able to be easily anticipated and the operation of putting into the visual field the part to be observed by changing the visual field will be made easy.

Figure 20:
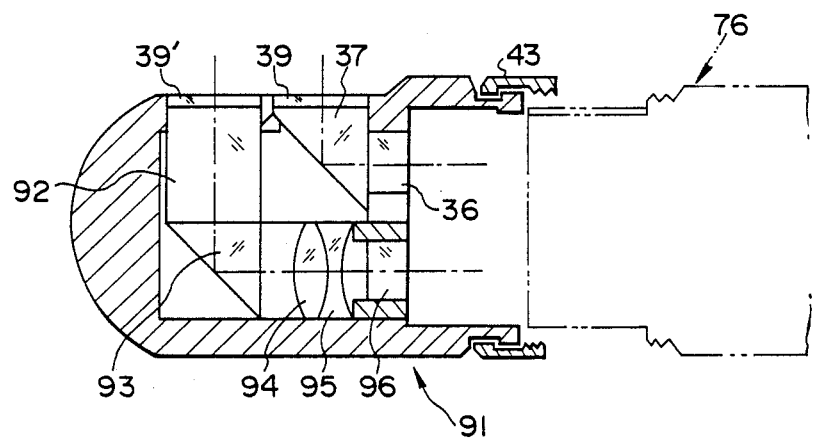
FIG. 20 is a sectioned view showing the structure of an adapter fittable to the third embodiment.

Now, such tip adapter 91 as is shown, for example, in FIG. 20 can be fitted also to this stereo-endoscope 72. In this adapter 91, in the adapter 24 shown in FIG. 17, a visual field changing optical system comprising an optical rod 92, prism 93, lenses 94 and 95 and optical rod 96 is arranged instead of the light guide 41. This visual field changing optical system is of substantially the same optical characteristics as of the visual field changing optical system by the prism 377 and optical rod 36. By the way, the prism 92 is covered on the end surface with a cover glass 39'.

Even in case this tip adapter 91 is fitted, as the direction in which a parallax is made intersects at right angles with the R/L rotary axis, the direction in which the visual field is moved by the curving operation will be easy to anticipate.

BY the way, in case the adapter 91 is not fitted, a ring-like adapter 98 shown by the two-point chain lines in FIG. 19 may be fitted to prevent dirts from being deposited on the screw part 44.

When an illuminating light from an ordinary light source apparatus (for example, 53) is fed to one light guide (for example, 81), the above mentioned third embodiment will be able to be used as an ordinary one-eye endoscope. In the case of using it as a one-eye endoscope, the adaper 24 shown in FIG. 7 will be able to be used.

Also, a light guide transmitting exclusively an illuminating light can be further provided in the third embodiment.

By the way, in the above described respective embodiments, the endoscope provided with the curvable part which can be curved in four directions of the R/L directions and U/D directions has been explained. However, it is apparent that the present invention is not limited to it and can be applied also to the case of an endoscope curvable only in the R/L direction or U/D direction.

Other different embodiments can be formed also by combining the above described respective embodiments.

What is claimed is:

1. A fiber-scope comprising:
an insertable part consisting of a rigid tip part, a curvable tube part adjacent to said tip part and rotatably connecting a plurality of articulated frames through at least a pair of opposed pivoting parts and a long flexible tube part adjacent to said curvable tube part and consisting of a long flexible tube part;
at least a pair of curving wires secured respectively in one end part near the front end of said curvable tube part, inserted along said respective pivoting parts in the lengthwise direction of said curvable tube part and connected at the respective other ends to a curving mechanism provided in said operating part;
an objective optical system secured within said tip part;
an image guide means secured on one end surface to the focal plane of said objective optical system, transmitting an optical image formed on said end surface to the other end surface and having a flexibility;
an eyepiece part provided with an eyepiece window formed as opposed to said other end surface of said image guide means;
a light guide means inserted through said insertable part, transmitting an illuminating light fed to one end surface, emitting the illuminating light from the other end surface fixed to said tip part and having a flexibility; and
a fixing means for fixing said both means to said tip part so that the line connecting the centers of the tip side end surfaces of said image guide means and said light guide means and the line connecting said pair of pivoting parts may be parallel/intersect at right angles with each other,
wherein said image guide means and said light guide means are inserted through said curvable tube part while the part adjacent to the end part fixed by said fixing means is displaced rotatably around the center axis of said tip part to be displaced from said pivoting part.

2. A fiber-scope according to claim 1 wherein said curvable tube part pivots said articulated frame with said pair of pivoting parts and also pivots said articulated frame with a pair of pivoting parts intersecting at right angles with said pair of pivoting parts.

3. A fiber-scope according to claim 1 or 2 wherein an optical adapter provided with an observing optical system and illuminating light optical system as opposed to the end surfaces of said objective optical system and light guide means is fittable to said tip part.

4. A fiber-scope according to claim 3 wherein said optical adapter is of a side viewing type in which the optical axis direction of said observing optical system is directed sidewise to intersect at right angles with the axis of said tip part.

5. An electronic endoscope comprising:
an insetable part consisting of a rigid tip part, a curvable tube part adjacent to said tip part and rotatably connecting a plurality of articulated frames through at least a pair of opposed pivoting parts and a long flexible tube part adjacent to said curvable tube part and consisting of a long flexible tube part;
at least a pair of curving wires secured respectively in one end part near the front end of said curvable tube part, inserted along said respective pivoting parts in the lengthwise direction of said curvable tube part and connected at the respective other ends to a curving mechanism provided in said operating part;
an objective optical system secured within said tip part;
a solid state imaging device arranged in the focal plane of said objective optical system and provided with a photoelectrically converting function;
a flexible signal cable connected in one end part to said solid state imaging device and inserted through said insertable part;
a flexible light guide inserted through said insertable part, transmitting an illuminating light fed to one end surface and emitting the illuminating light from the other end surface fixed to said tip part; and
a fixing means for fixing said objective optical system and light guide to said tip part so that the line connecting the center of said objective optical system and the center of said other end surface of said light guide and the line connecting said pair of pivoting parts may be parallel/vertical to each other, wherein said signal cable and light guide in the part adjacent to the end part fixed by said fixing means are rotatably displaced around the center axis of said tip part and are inserted through said curvable tube part as displaced from said pivoting parts.

6. An electronic endoscope according to claim 5 wherein said curvable tube part pivots said articulated frame with said pair of pivoting parts and also pivots said articulated frame with a pair of pivoting parts intersecting at right angles with said pair of pivoting parts.

7. An electronic endoscope according to claim 6 wherein an optical adapter provided with an observing optical system and illuminating light optical system as opposed to the end surfaces of said objective optical system and light guide means is fittable to said tip part.

8. An electronic endoscope according to claim 7 wherein said optical adapter is of a side viewing type in which the optical axis direction of said observing optical system is directed sidewise to intersect at right angles with the axis of said tip part.

9. A stereo-observing endoscope comprising:
an insertable part consisting of a rigid tip part, a curvable tube part adjacent to said tip part and rotatably connecting a plurality of articulated frames through at least a pair of opposed pivoting parts and a long flexible tube part adjacent to said curvable tube part and consisting of a long flexible tube part;
at least a pair of curving wires secured respectively in one end part near the front end of said curvable tube part, inserted along said respective pivoting parts in the lengthwise direction of said curvable tube part and connected at the respective other ends to a curving mechanism provided in said operating part;
first and second objective optical sYstems secured within said tip part so that the line connecting said pair of pivoting parts and the line connecting the two optical axes may be parallel/intersect at right angles with each other;
first and second image guides arranged respectively on one end surface in the respective focal planes of said first and second objective optical systems, inserted as displaced from said pivoting parts at least within said curvable tube part, capable of transmitting an optical image and having a flexibility;
first and second beam splitters arranged as opposed respectively to the other end surfaces of said first and second image guides;
first and second light guides respectively arranged on one end surface as opposed to the respective one end surface of said first and second beam splitter and capable of transmitting an illuminating light; and
an eyepiece part having first and second eyepiece optical systems arranged as opposed to the respective other end surfaces of said first and second beam splitters.

10. A stereo-observing endoscope according to claim 9 wherein said curvable tube part pivots said articulated frame with said pair of pivoting parts and also pivots said articulated frame with a pair of pivoting parts intersecting at right angles with said pair of pivoting parts.

11. A stereo-observing endoscope according to claim 9 or 10 wherein an optical adapter provided with an observing optical system and illuminating light optical system as opposed to the end surfaces of said objective optical system and light guide means is fittable to said tip part.

12. A stereo-observing endoscope according to claim 11 wherein said optical adapter is of a side viewing type in which the optical axis direction of said observing optical system is directed sidewise to intersect at right angles with the axis of said tip part.

13. A stereo-observing endoscope according to claim 9 further comprising a light source means feeding an illuminating light alternately to the respective other end surfaces of said first and second light guides.

* * * * *